United States Patent
Erhard (10) Patent No.: US 10,238,354 B2
(45) Date of Patent: Mar. 26, 2019

(54) GENERATING A BREAST PARAMETER MAP

(71) Applicant: KONINKLIJKE PHILIPS N.V., Eindhoven (NL)

(72) Inventor: Klaus Erhard, Hamburg (DE)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 107 days.

(21) Appl. No.: 15/114,438

(22) PCT Filed: Feb. 4, 2015

(86) PCT No.: PCT/EP2015/052344
§ 371 (c)(1),
(2) Date: Jul. 27, 2016

(87) PCT Pub. No.: WO2015/118033
PCT Pub. Date: Aug. 13, 2015

(65) Prior Publication Data
US 2016/0338660 A1 Nov. 24, 2016

(30) Foreign Application Priority Data

Feb. 4, 2014 (EP) .................................. 14153740

(51) Int. Cl.
*G06K 9/00* (2006.01)
*G06K 9/62* (2006.01)
(Continued)

(52) U.S. Cl.
CPC ............ *A61B 6/502* (2013.01); *A61B 6/4241* (2013.01); *A61B 6/461* (2013.01); *A61B 6/5217* (2013.01);
(Continued)

(58) Field of Classification Search
None
See application file for complete search history.

(56) References Cited

U.S. PATENT DOCUMENTS 5,572,565 A 11/1996 Abdel-Mottaleb
2003/0211036 A1 11/2003 Degani
(Continued)

FOREIGN PATENT DOCUMENTS

EP 2238905 10/2010
WO 2006/055251 5/2006
(Continued)

OTHER PUBLICATIONS

Chen et al., Cone-beam volume CT breast imaging: Feasibility study, Med. Phys. 29 (5), May 2002, pp. 755-770.*
(Continued)

*Primary Examiner* — Randolph I Chu
(74) *Attorney, Agent, or Firm* — Larry Liberchuk (57) ABSTRACT

The present invention relates to a medical imaging device for generating a breast parameter map in order to improve mammographic images. The medical imaging device comprises an image unit, a raster unit, a definition unit, a generating unit, and a provision unit. The image unit is configured to provide image data of a breast. The raster unit is configured to provide a predefined raster with several subportions, which is preferably predefined based on a predefined coordinate system relative to predefined body characteristics of a standard breast. The definition unit is configured to define several subvolumes in the breast according to the subportions of the raster, preferably by identification of body characteristics in the image data for adaption of the raster subportions to the image data. The generating unit is configured to generate a breast parameter per breast subvolume. The provision unit is configured to provide a breast parameter per breast subvolume in a breast parameter map, wherein each breast parameter is allocated to its breast subvolume.

20 Claims, 4 Drawing Sheets

(51) Int. Cl.
*A61B 6/00* (2006.01)
*G06T 7/00* (2017.01)

(52) U.S. Cl.
CPC .. *G06T 7/0012* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/30068* (2013.01)

(56) References Cited

U.S. PATENT DOCUMENTS

| | | |
|---|---|---|
| 2011/0013819 A1 | 1/2011 | Raundahl |
| 2011/0280465 A1 | 11/2011 | Wehnes |
| 2012/0157819 A1 | 6/2012 | Jerebko |
| 2014/0327702 A1* | 11/2014 | Kreeger ............. G06T 11/006 345/634 |
| 2014/0355840 A1* | 12/2014 | Pearson Peyton .... G06T 7/0014 382/115 |
| 2015/0052471 A1* | 2/2015 | Chen ................. A61B 6/025 715/771 |
| 2016/0235380 A1* | 8/2016 | Smith ................ A61B 6/025 |
| 2017/0340300 A1* | 11/2017 | Kreeger ............. G06F 3/04847 |
| 2018/0008220 A1* | 1/2018 | Boone ............... A61B 6/4417 |

FOREIGN PATENT DOCUMENTS

| | | |
|---|---|---|
| WO | 2012/080914 | 6/2012 |
| WO | 2012/107057 | 8/2012 |
| WO | 2012/116746 | 9/2012 |

OTHER PUBLICATIONS

Chen B et al: "Cone-Beam Volume CT Breast Imaging: Wavelet Analysis-based Multi-resolution Reconstruction and De-noising Technique", Proceedings of SPIE, SPIE—International Society for Optical Engineering, US, vol. 4682, May 1, 2002.

Fredenberg E et al: "Measurement of breast-tissue x-ray attenuation by spectral mammography: first results on cyst fluid", Physics in Medicine and Biology, Institute of Physics Publishing, Bristol GB, vol. 58, No. 24, Nov. 20, 2013.

Karemore, et al., "Anisotropic Diffusion Tensor Applied to Temporal Mammograms: An Application to Breast Cancer Risk Assessment", 2010 Annual International Conference of the IEEE Engineering in Medicine and Biology.

Saidin, et al., "Computer Aided Detection of Breast Density and Mass, and Visualization of Other Breast Anatomical Regions on Mammograms Using Graph Cuts", Computational and Mathematical Methods in Medicine, vol. 2013, Article ID 205384.

Brandt, et al., "An Anatomically Oriented Breast Coordinate System for Mammogram Analysis", IEEE Transactions on Medical Imaging, vol. 30, No. 10, Oct. 2011.

* cited by examiner

GENERATING A BREAST PARAMETER MAP

CROSS REFERENCE TO RELATED APPLICATIONS

This application is the U.S. National Phase application under 35 U.S.C. § 371 of International Application No. PCT/EP2015/052344, filed Feb. 4, 2015, published as WO 2015/118033 on Aug. 13, 2015, which claims the benefit of European Patent Application Number 14153740.7 filed Feb. 4, 2014. These applications are hereby incorporated by reference herein.

FIELD OF THE INVENTION

The present invention relates to mammography. In particular, the present invention relates to a medical imaging device for generating a breast parameter map, a medical imaging method for generating a breast parameter map, a computer program element for controlling such device and a computer readable medium having stored such computer program element.

BACKGROUND OF THE INVENTION

Mammography information is used for example for breast cancer screening. During mammography a breast under examination is mechanically compressed and subsequently a radiographic image of the flattened breast tissue is acquired. WO 2012/080914 A1 discloses a method for providing mammography information about an object of interest with the following steps: acquiring first and second image data, performing a dual energy basis material decomposition and deriving a density information of the tissue structure of the region of interest from the decomposed basis material image data, and providing the density information to a user. It has been shown that the evaluation of mammographic images is generally difficult and leads to unclear results.

CHEN B ET AL: "Cone-Beam Volume CT Breast Imaging: Wavelet Analysis-based Multi-resolution Reconstruction and De-noising Technique", PROCEEDINGS OF SPIE, SPIE—INTERNATIONAL SOCIETY FOR OPTICAL ENGINEERING, US, vol. 4682, 1 May 2002 (2002 May 1), discloses a wavelet analysis-based multi-resolution cone-beam volume CT breast imaging technique that is adaptive for high-resolution and ultra-high resolution reconstructions. Wavelet analysis-based de-noising techniques are employed to improve image quality and further reduce the required absorbed dose.

US 2012/157819 A1 discloses a method which visualizes a tissue region. The method includes the following steps: inserting the tissue region into the capturing region of a first imaging modality, with the tissue region assuming a first shape; capturing the interior of the tissue region by the first imaging modality; establishing a first image volume of the interior of the tissue region when it assumes the first shape; and first transforming of the first image volume into a second image volume, which represents a surface and interior regions of the tissue when the tissue region assumes a second shape.

FREDENBERG E ET AL: "Measurement of breast-tissue x-ray attenuation by spectral mammography: first results on cyst fluid", PHYSICS IN MEDICINE AND BIOLOGY, INSTITUTE OF PHYSICS PUBLISHING, BRISTOL GB, vol. 58, no. 24, 20 Nov. 2013 discloses a method to measure x-ray attenuation of tissue samples using a prototype photon-counting spectral mammography unit. The method was applied to measure the attenuation of 50 samples of breast cyst fluid and 50 samples of water. Spectral (energy-resolved) images of the samples were acquired and the image signal was mapped to equivalent thicknesses of two known reference materials, which can be used to derive the x-ray attenuation as a function of energy.

SUMMARY OF THE INVENTION

Hence, there may be a need to provide a medical imaging device, which provides mammographic images that are easier to assess.

The object of the present invention is solved by the subject-matters of the independent claims, wherein further embodiments are incorporated in the dependent claims. It should be noted that the following described aspects of the invention apply also for the medical imaging device, for the medical imaging method, for the computer program element, and for the computer readable medium.

According to the present invention, a medical imaging device for generating a breast parameter map is presented. The medical imaging device comprises an image unit, a raster unit, a definition unit, a generating unit, and a provision unit.

The image unit is configured to provide image data of a breast. The image unit may be an X-ray device, an ultrasound device, a MR device, a CT device, a PET device, a SPECT device and/or else and/or combinations thereof. In an example, the image unit is an X-ray device with an X-ray source and an X-ray detector. The image data of the breast might be a mammogram in cranio-caudal (CC) view, in medio-lateral oblique (MLO) view and/or another view. Preferably, the image data of the breast is acquired in at least two angles of view. A 3D breast volume examined by the X-ray device appears as 2D projection in a mammogram.

The raster unit is configured to provide a predefined spatial raster with several subportions. The raster might be radial, grid-shaped or shaped as a pie chart. The raster is preferably predefined based on a predefined coordinate system relative to predefined body characteristics of a standard breast.

The term "predefined points of the raster" might relate to the original and intersection of the axes, the position or direction of the axes or else.

The term "predefined body characteristics" might relate to a mammilla, a pectoralis muscle, a pectoralis/chest wall, a breast contour, an axilla and/or combinations thereof.

The definition unit is configured to define several subvolumes in the breast according to the subportions of the raster and is configured to define an identification of body characteristics in the image data and a segmentation of the image data according to raster subportions and identified body characteristics. In other words, the subportions of the raster segment the breast volume into several subvolumes. The defining comprises an identification of body characteristics in the image data and a segmentation of the image data according to raster subportions and identified body characteristics.

The generating unit is configured to generate a breast parameter per breast subvolume. The subvolumes of the breast are then used to generate at least one breast parameter per breast subvolume. The breast parameters can be computed from the image data or be evaluated by other means and devices. The breast parameter can be one or more of the following properties: breast density, glandular volume fraction, glandular tissue volume, breast tissue volume, adipose tissue volume, adipose volume fraction, water content or combinations thereof. The breast parameter(s) can also be stiffness or elasticity parameters. The breast parameter(s) can further be related to a material decomposition of the breast into e.g. aluminium and polymethyl methacrylate (PMMA) from a mammogram, which is acquired by spectral imaging. A spectral mammogram can be acquired for example on a mammography unit with a photon-counting detector with at least two energy bins such as the Philips MicroDose SI system, which enables the separation of a spectral mammogram into a high-energy and a low-energy mammogram for subsequent material decomposition.

The provision unit is configured to provide a breast parameter per breast subvolume in a breast parameter map, wherein each breast parameter is allocated to its breast subvolume. The provision unit preferably comprises a display to show the breast parameter map. In an example, the breast parameter(s) per region can be visualized by colour coding, grey shades, patterns, symbols, numbers, letters and/or in text form.

In a further example of the present invention, a medical imaging method for generating a breast parameter map is presented. It comprises the following steps:

a) providing image data of a breast,
b) providing a predefined raster with several subportions,
c) defining several subvolumes in the breast according to the subportions of the raster, wherein the defining comprises an identification of body characteristics in the image data and a segmentation of the image data according to raster subportions and identified body characteristics,
e) generating a breast parameter per breast subvolume, and
f) providing a breast parameter per breast subvolume in a breast parameter map, wherein each breast parameter is allocated to its breast subvolume.

In a further example of the present invention, a medical imaging computer program for generating a breast parameter map is presented, wherein the computer program comprises program code means for causing a medical imaging device as defined in the independent device claim to carry out the steps of the medical imaging method as defined in the independent method claim, when the computer program is run on a computer controlling the object tracking device.

According to an aspect of the present invention, the subportions of the predefined raster segment the breast volume into several subvolumes. The raster is preferably based on a predefined coordinate system relative to predefined body characteristics. A breast parameter is generated for each subvolume and provided in a breast parameter map, wherein each breast parameter is allocated to its breast subvolume. Thereby, a breast parameter visualization is created, which makes it easier and clearer to assess the information and in particular to assess the breast condition per breast subvolume. Further, this information combination of condition and location is extremely valuable and still also easy to store, to report and to handle. In particular, a standardized report is enabled which allow an automatic evaluation of large data amounts for e.g. comparisons over the time (longitudinal parameter tracking) or the population (epidemiological studies).

In one exemplary embodiment, this invention proposes to combine the information of the spatial distribution of dense tissue acquired from ipsilateral 2D mammograms (CC+MLO views) to generate estimates of average density values in 3D subvolumes of the breast, which are annotated as subregions in a breast parameter map. The density (percentage) or glandular volume (ml) values can be presented colour-coded on a continuous scale with an additional overlay of the local ACR density category (I-IV). As the breast is de-compressed and re-compressed between the CC and the MLO acquisition, the corresponding tissue areas have to be identified prior to computing averaged values by using for example a breast coordinate system given by the radial distance to the nipple and the orthogonal distance to the pectoralis/chest wall in each view. As a result, e.g. a reporting of the spatial distribution of the glandular tissue volume and the local breast density in a breast parameter map is provided.

It shall be understood that the medical imaging device for generating a breast parameter map, the medical imaging method for generating a breast parameter map, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
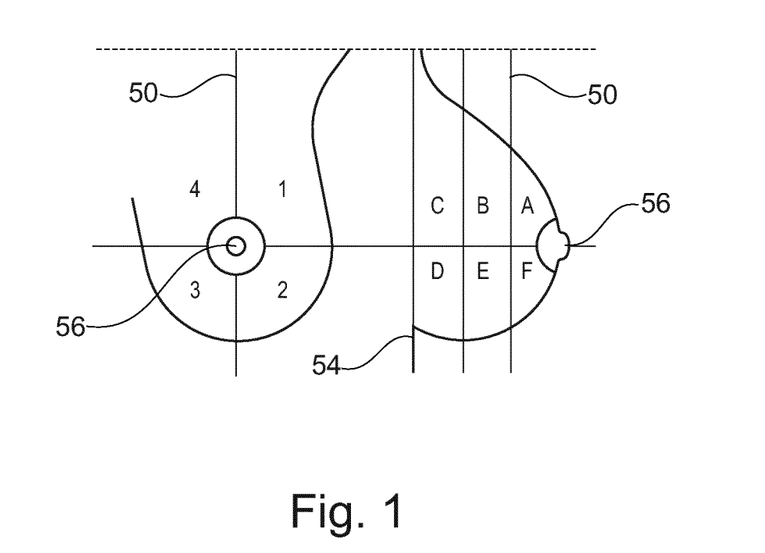
FIG. 1 shows a schematic drawing of an example of a predefined raster for a breast.
Figure 2:
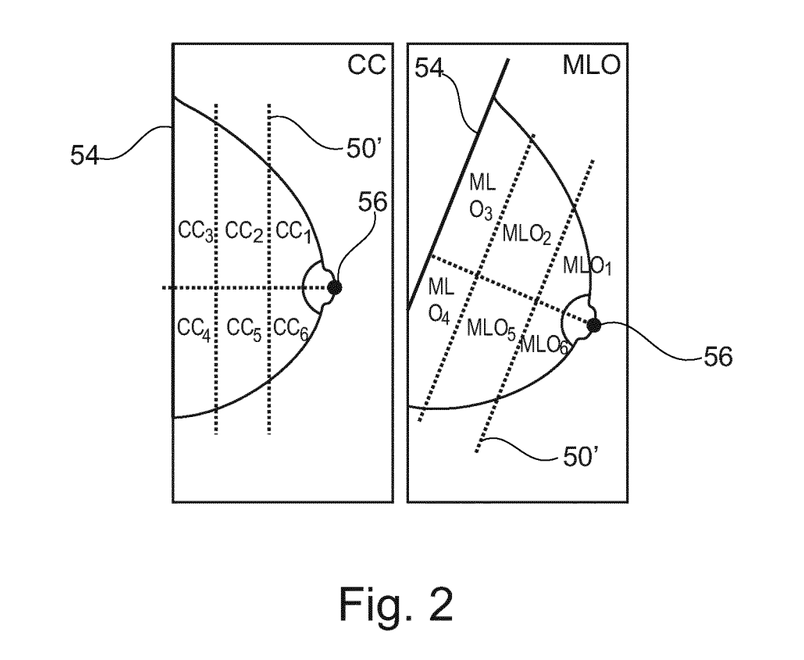
FIG. 2 shows a schematic drawing of an image data of a breast with a raster.
Figure 3:
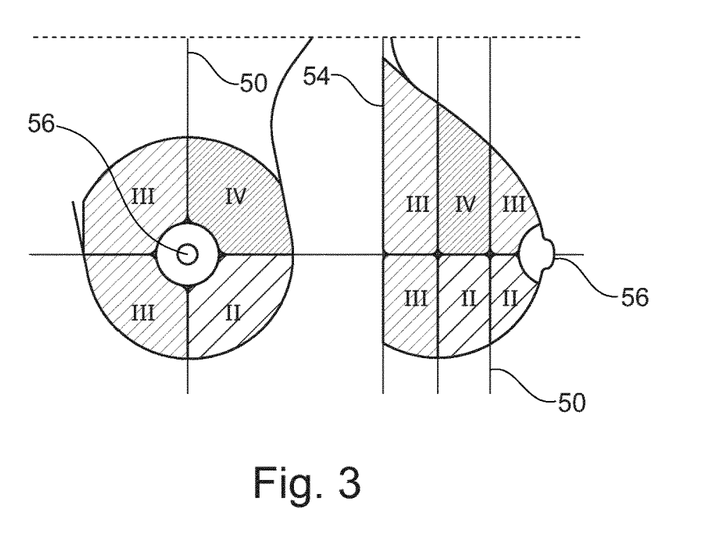
FIG. 3 shows a schematic drawing of an example of a breast parameter map.

FIGS. 1 to 3 show schematically and exemplarily a medical imaging method for generating a breast parameter map. Step-by-step, FIG. 1 shows schematically and exemplarily a predefined spatial raster 50 for a breast in a top view and a side view. The raster 50 is predefined based on a predefined coordinate system relative to predefined body characteristics of a breast.

Here, in the top view, the predefined raster 50 is based on a coordinate system with having the origin of both axes in the mammilla or nipple 56. In other words, the axes of the coordinate system resemble to crosshairs with the nipple 56 as centre. The axes form four subportions of the raster 50. These subportions are characterised by numbers from 1 to 4 starting above right and going clockwise.

The raster 50 is manually or automatically correctly set into the image data relative to predefined body characteristics. This means, a predefined body characteristic as e.g. the nipple 56 is detected in the image data and the e.g. centre of the raster 50 is set on the nipple 56.

The body characteristics for the coordinate system may also be the axilla, the pectoralis muscle itself, the breast contour, which means the skin line and/or combinations thereof. Therefore, the coordinate system may also be otherwise arranged relative to the body characteristics. Further, the predefined raster 50 can comprise more or other subportions, which can also be otherwisly formed and/or arranged. For example, circular subportions can be arranged radially around the nipple 56 or the subportions can be shaped as a pie chart around the nipple 56. Also a pixel-by-pixel mapping using the nipple-pectoralis coordinate system could be used to generate an approximate 3D glandularity map on a reference breast diagram.

In the side view, the predefined spatial raster 50 is based on a coordinate system with having the pectoralis muscle/chest wall 54 as vertical axis intersecting the horizontal axis through the nipple 56. The axes form six subportions of the raster 50. These subportions are characterised by letters A to F starting above right and going above to the left, and down from left to right.

In an example, the raster 50 is a standard raster 50 for a standard breast, which can be adapted to a particular breast shown in the image data. Therefore, predefined points of the standard raster 50 are mapped to predefined body characteristics shown in the image data. In other words, the raster 50 is not only manually or automatically correctly set into the image data relative to predefined body characteristics, but also manually or automatically adapted to the particular breast shown in the image data, which means the raster subportions are adapted and/or deformed to match this particular breast.

FIG. 2 shows image data of an actual breast acquired and/or provided by an image unit, here a drawing of a mammography image of an X-ray device. The image data of the breast are acquired and provided in two angles of view, namely cranio-caudal (CC) and mediolateral-oblique (MLO). FIG. 2 also shows a projection 50' of the raster 50 into the mammograms with corresponding subportions, which define several subvolumens being represented by the projected areas $CC_1$ to $CC_6$ and $MLO_1$ to $MLO_6$ in the mammograms. The subvolumes of the breast are used to generate at least one breast parameter per breast subvolume. The breast parameter can be one or more of the following quantitities: breast density, glandular volume fraction, glandular tissue volume, breast tissue volume, adipose tissue volume, adipose volume fraction, water content or combinations thereof. The breast parameter can also be a number and/or size of certain features in the subvolume such as the number and/or size of calcifications, lesions, cysts, architectural distortions, asymmetries, spiculated masses or combinations thereof.

The breast parameter(s) can also be related to a material decomposition of the breast into two base materials as e.g. aluminium and polymethyl methacrylate (PMMA) from a mammogram, which is acquired by spectral imaging. A spectral mammogram can be acquired for example on a mammography unit with a photon-counting detector with at least two energy bins such as the Philips MicroDose SI system.

As shown in FIG. 3, the breast parameter per breast subvolume is then provided in a breast parameter map, wherein each breast parameter is allocated to its breast subvolume. The breast parameter map resembles to the view according to FIG. 1, but now, the breast parameters for each subvolume are graphically allocated to the respective breast subvolume. The breast parameter(s) can be visualized e.g. by colour coding, grey shades, patterns, symbols, numbers, letters, text form and/or combinations thereof. As show in FIG. 3, the breast subvolumes according to FIG. 1 are characterized by grey shades and roman numbers representing two different breast parameters per breast subvolume.

Figure 4:
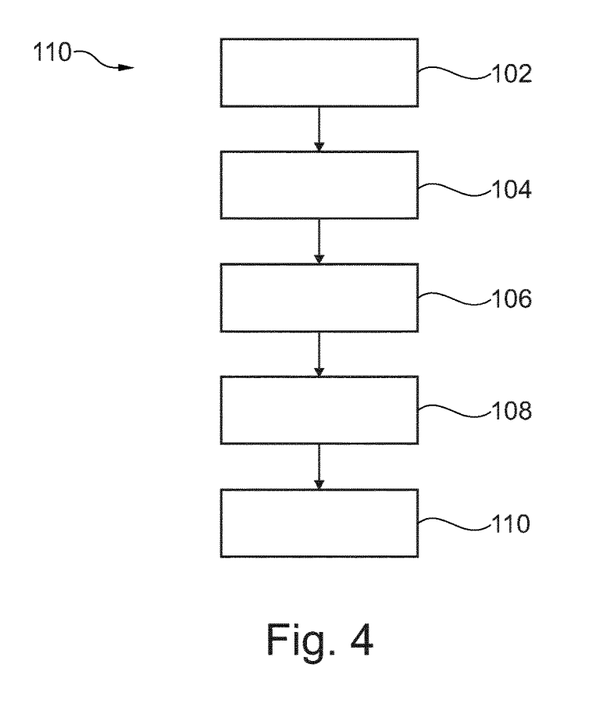
FIG. 4 shows basic steps of an example of a method for generating a breast parameter map.

FIG. 4 shows a schematic overview of method steps for generating a breast parameter map. It comprises the following steps, not necessarily in this order:

In a first step 102, image data of a breast are provided, in a second step 104, a predefined raster 50 with several subportions is provided, in a third step 106, several subvolumes are defined in the breast according to the subportions of the raster 50, in a fourth step 108, a breast parameter per breast subvolume is generated, and in a fifth step 110, a breast parameter per breast subvolume is provided in a breast parameter map, wherein each breast parameter is allocated to its breast subvolume.

The method may comprise an identification of body characteristics in the image data and a segmentation of the image data according to raster subportions and identified body characteristics as explained in the following. The predefined raster 50 of step 104 is an ideal or a standard raster 50 for a standard breast, which can be adapted in or after step 106 to a particular breast shown in the image data. Thereto, predefined points of the standard raster 50 are mapped to predefined body characteristics shown in the image data. In other words, the raster 50 is not only manually or automatically correctly set into the image data relative to predefined body characteristics, but also manually or automatically adapted to the particular breast shown in the image data, which means the raster subportions are adapted and/or deformed to match this particular breast. The adaption of the raster 50 can further be based on information concerning the acquisition geometry of the image data, as e.g. the projection geometry of a mammography examination.

In this exemplary embodiment, the projection area of the selected annotation areas A-F and 1-4 in FIG. 1 have to be identified in the CC and MLO mammograms of FIG. 2. To this end, a breast-coordinate system is used, which is defined by the breast nipple 56 and the pectoralis muscle/chest wall 54 as indicated with the broken lines in FIG. 2. Both, pectoralis muscle/chest wall 54 and nipple 56 can be detected automatically in the mammogram. The corresponding areas in the mammograms are denoted with $CC_1$-$CC_6$ and $MLO_1$-$MLO_6$, respectively. In this example, the line heading to the nipple 56 in the CC view of FIG. 2 separates the breast into a left and a right half, while the line heading to the nipple 56 in the MLO view separates the breast into an upper and a lower half.

For the ML-view, the glandular volume in subvolume A of the raster equals the measured glandular volume in area $ML_1$, and similar equalities hold for subvolumes B-F of the raster. For the MLO view, it is assumed that these equations yield an approximation for the unknown glandular volumes in the raster subvolumes A-F. Then, the remaining unknown glandular volumes $G_1$ to $G_4$ in the subvolumes 1-4 of the raster satisfy the system of linear equations:

$$G_1+G_2=CC_1+CC_2+CC_3$$

$$G_3+G_4=CC_4+CC_5+CC_6$$

$$G_1+G_4=MLO_1+MLO_2+MLO_3$$

$$G_3+G_2=MLO_4+MLO_5+MLO_6$$

with a singular system matrix $$A = \begin{pmatrix} 1 & 1 & 0 & 0 \\ 0 & 0 & 1 & 1 \\ 1 & 0 & 0 & 1 \\ 0 & 1 & 1 & 0 \end{pmatrix}$$

for the unknown glandular volumes $G_1$-$G_4$. Therefore, an approximate solution for $G_1$-$G_4$ can be computed with the pseudo-inverse matrix of A, e.g.

$$\begin{pmatrix} G_1 \\ G_2 \\ G_3 \\ G_4 \end{pmatrix} = A^+ \begin{pmatrix} CC_1 + CC_2 + CC_3 \\ CC_4 + CC_5 + CC_6 \\ MLO_1 + MLO_2 + MLO_3 \\ MLO_4 + MLO_5 + MLO_6 \end{pmatrix},$$

with $$A^+ = \frac{1}{8} \begin{pmatrix} 3 & -1 & 3 & -1 \\ 3 & -1 & -1 & 3 \\ -1 & 3 & -1 & 3 \\ -1 & 3 & 3 & -1 \end{pmatrix}$$

In this way, e.g. a breast parameter map with either glandular volume or breast density annotation can be generated by colour-coding the annotation areas with the computed values as depicted in FIG. 3. As a result, the spatial distribution of the glandular tissue volume and the local breast density is reported in a breast parameter map. In this way, e.g. the distribution of the glandular volume can be easily depicted and tracked over time in a standardized breast parameter map.

Figure 5:
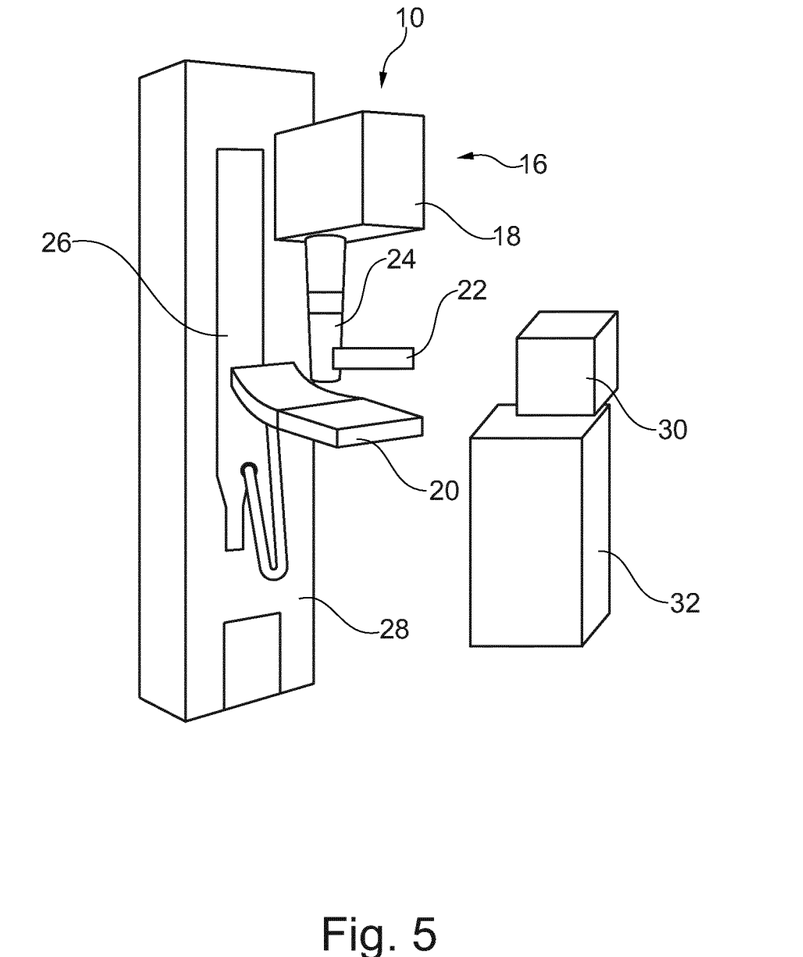
FIG. 5 shows a schematic drawing of an example of an X-ray imaging system.

A medical imaging device for generating a breast parameter map is shown in the following. In detail, FIG. 5 shows a schematic drawing of an example of an X-ray imaging system 10 for providing mammography information. The X-ray imaging system 10 comprises an image unit 16 with an X-ray source 18 and an X-ray detector 20. The X-ray image unit 16 is adapted to provide mammography image data of a breast. The example shown is a so-called stand-up investigation system where, for example, a patient in an upright position can stand while, for example, the breast is examined. Therefore, the X-ray detector 20 is provided as a sort of a paddle or small table upon which a breast can be received. Further, a moveable compression paddle 22 is provided with an adaptable distance to the detector 20 in order to be able to act with a desired pressing force on the breast arranged detector 20 and the compression paddle 22. Therefore, the compression paddle 22 is attached to an adjusting mechanism 24 allowing the necessary movement of the compression paddle.

The X-ray source 18 is generating X-ray radiation emanating towards the detector 20. Further, the X-ray source 18 and the detector 20 are attached to an adjustable support 26 allowing for a vertical adjustment such that the height of the detector can be adapted to different sizes of the patient. Further, a rotational movement is possible to acquire X-ray images not only in a vertical direction, but also in a direction with an angle to the vertical direction, such as 30° or any freely chooseable angulation as well as an X-ray viewing direction in a horizontal way. Further, a base 28 is provided which is securely fixed to a floor of an examination room, for example.

In addition to the X-ray image unit 16, the X-ray imaging system 10 also comprises a provision unit 30 with a display 34 provided on a separate base 32. It is noted that any data connection is not further shown, which data connection can be provided as wire connection or wireless connection between the respective parts of the system 10. It must be further noted that besides the shown stand-up investigation system, also other types for X-ray imaging are possible, for example moveable or stationary X-ray imaging systems or X-ray imaging systems with a table upon which a patient can be received in order to acquire X-ray images while the patient is lying on the table, for example facing downwards.

The image data of the breast can also be acquired by an ultrasound device, a MR device, a CT device, a PET device, a SPECT device and/or else.

Figure 6:
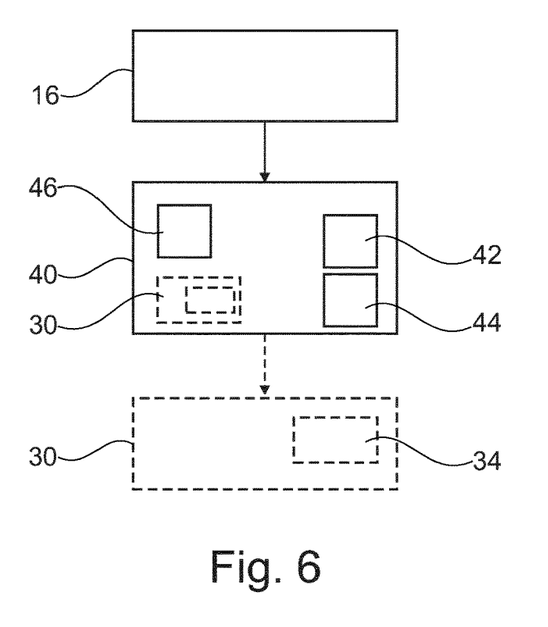
FIG. 6 shows a schematic drawing of an example of an image unit, a processing unit and a provision unit.

FIG. 6 shows a schematic drawing of an example of an image unit 16 and a processing unit 40. The exemplary processing unit 40 comprises a raster unit 42, a definition unit 44 and a generating unit 46. An exemplary provision unit 30 can be arranged either in the processing unit 40 or separate from the processing unit 40. The provision unit 30 comprises e.g. a display 34. The image unit 16 is configured to provide image data of a breast, the raster unit 42 is configured to provide a predefined raster with several subportions. The definition unit 44 is configured to define several subvolumes in the breast according to the subportions of the raster 50. The subvolumes are preferably adapted to the actual image data. The generating unit 46 is configured to generate a breast parameter per breast subvolume, and the provision unit 30 is configured to provide a breast parameter per breast subvolume in a breast parameter map, wherein each breast parameter is allocated to its breast subvolume.

Figure 7:
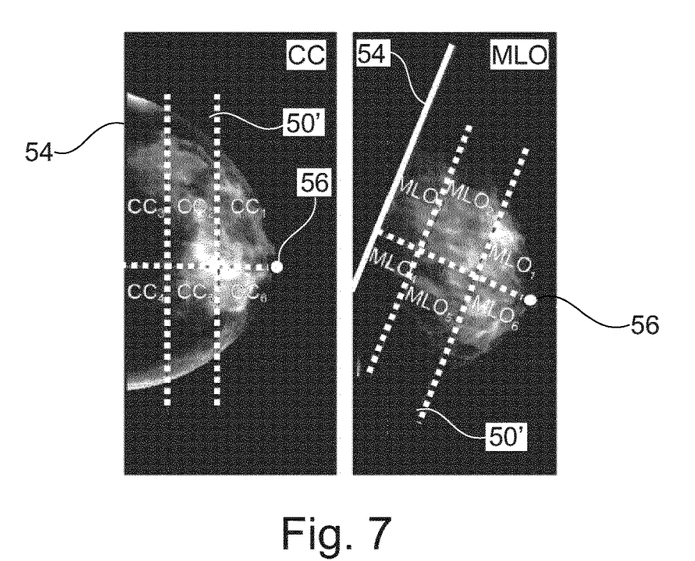
FIG. 7 shows an example of an image data of a breast with a raster.

FIG. 7 shows image data of an actual breast acquired and/or provided by an image unit, here a mammography image of an X-ray device. The image data of the breast are acquired and provided in two angles of view, namely craniocaudal (CC) and mediolateral-oblique (MLO). FIG. 7 also shows the projection 50' of the raster 50 with subportions, which define several subvolumes of the breast and are projected onto the area segments $CC_1$-$CC_6$ and $MLO_1$-$MLO_6$ in the CC and MLO mammogram, respectively.

In another exemplary embodiment of the present invention, a computer program or a computer program element is provided that is characterized by being adapted to execute the method steps of the method according to one of the preceding embodiments, on an appropriate system. The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention. Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging device for generating a breast parameter map, the device comprising:
    an image device; and
    at least one electronic processor programmed to:
        control the image device to provide image data of a particular breast,
        provide a predefined raster with several subportions, wherein the subportions segment the breast volume,
        define several subvolumes in the particular breast according to the subportions of the raster by defining an identification of body characteristics in the image data of the particular breast and segmenting the image data of the particular breast into said subvolumes by deforming the raster subportions according to identified body characteristics of the particular breast,
        generate a breast parameter per breast subvolume, and
        control a display device to display a breast parameter per breast subvolume in a breast parameter map, wherein each breast parameter is allocated to its breast subvolume.

2. The medical imaging device according to claim 1, wherein the image unit comprises an X-ray source and an X-ray detector.

3. A medical imaging method for generating a breast parameter map, comprising, with at least one electronic processor:
    controlling an imaging device to acquire image data of a breast,
    providing a predefined raster with several subportions, wherein the subportions segment the breast volume,
    defining several subvolumes in the breast according to the subportions of the raster, wherein the defining comprises an identification of body characteristics in the image data and a segmentation of the image data into said subvolumes by deforming raster subportions according to identified body characteristics,
    generating a breast parameter per breast subvolume, and
    controlling a display device to display a breast parameter per breast subvolume in a breast parameter map, wherein each breast parameter is allocated to its breast subvolume.

4. The medical imaging method according to claim 3, wherein the raster is radial, grid-shaped or shaped as a pie chart.

5. The medical imaging method according to claim 3, wherein the raster is based on a predefined coordinate system relative to predefined body characteristics.

6. The medical imaging method according to claim 3, wherein the image data of the breast is acquired in at least two angles of view.

7. The medical imaging method according to claim 3, wherein the image data of the breast are a CC and/or a MLO view.

8. The medical imaging method according to claim 3, wherein the breast parameter is one of breast density, glandular volume fraction, glandular tissue volume, breast tissue volume, adipose tissue volume, adipose volume fraction, water content, number of calcifications, lesions and/or cysts or combinations thereof.

9. The medical imaging method according to claim 3, wherein the breast parameter is related to a material decomposition of the breast into two base materials by spectral imaging.

10. The medical imaging method according to claim 9, wherein the two base materials are aluminium and PMMA.

11. The medical imaging method according to claim 3, wherein the breast parameter is derived by spectral imaging and is related to cyst fluid volume, solid lesion volume, muscle tissue volume, adipose tissue volume, glandular tissue volume or combinations thereof.

12. A medical imaging device for generating a breast parameter map, the device comprising:
    a display device;
    an X-ray imaging device comprising an X-ray source and an X-ray detector; and
    at least one electronic processor programmed to:
        control the X-ray imaging device to provide image data of a breast;
        define an identification of body characteristics in the image data of the breast;
        define a plurality of subvolumes in the breast according to subportions of a raster comprising a plurality of subportions that segment a breast volume wherein the subvolumes are defined by segmentation of the image data of the breast into said subvolumes by deforming the raster subportions according to the identified body characteristics of the breast;

generate a breast parameter per breast subvolume, and control the display device to display a breast parameter per breast subvolume in a breast parameter map, wherein each breast parameter is allocated to its breast subvolume.

13. The device according to claim 12, wherein the raster is displayed on the display device as radial, grid-shaped or shaped as a pie chart.

14. The device according to claim 12, wherein the raster is based on a predefined coordinate system relative to predefined body characteristics.

15. The device according to claim 12, wherein the X-ray imaging device is configured to acquire at least two angles of view of the breast.

16. The device according to claim 12, wherein the image data of the breast are a CC and/or a MLO view.

17. The device according to claim 12, wherein the breast parameter is one of breast density, glandular volume fraction, glandular tissue volume, breast tissue volume, adipose tissue volume, adipose volume fraction, water content, number of calcifications, lesions and/or cysts or combinations thereof.

18. The device according to claim 12, wherein the breast parameter is related to a material decomposition of the breast into two base materials by spectral imaging.

19. The device according to claim 12, wherein the two base materials are aluminium and PMMA.

20. The device according to claim 12, wherein the breast parameter is derived by spectral imaging and is related to cyst fluid volume, solid lesion volume, muscle tissue volume, adipose tissue volume, glandular tissue volume or combinations thereof.

* * * * *